US00PP10351P

United States Patent [19]

Kent

[11] Patent Number: Plant 10,351

[45] Date of Patent: Apr. 21, 1998

[54] BROMELIAD PLANT NAMED 'GUZ 218'

[75] Inventor: Jeffrey C. Kent, Vista, Calif.

[73] Assignee: Kent's Bromeliad Nursery, Inc., Vista, Calif.

[21] Appl. No.: 686,656

[22] Filed: Jul. 26, 1996

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—John H. Vynalek

[57] ABSTRACT

A Guzmania hybrid having bright red bracts, with the lower and uppermost bracts ascending and the intermediately positioned bracts splayed relative to the axis of the spike. Corollas protrude as bright yellow ovoid pod-like structures. Inflorescence is long lasting with the bract coloration having a high sheen.

1 Drawing Sheet

BACKGROUND OF THE INVENTION

This application relates to a newly developed interspecific hybrid Guzmania plant resulting from a planned breeding program which I conduct on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Included objects of my program are to produce plants which will be attractive to the consumer; which will develop reasonably rapidly under controlled conditions; and, retain for a long term, highly attractive and bright inflorescence; i.e., bract coloration, after being induced into the flowering stage. It is a specific object to provide a low maintenance plant which will be a long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by state-of-the-art tissue culture methods while continuing the distinctive characteristics of the plants through progressive clonal generations.

The plant of this disclosure was a selection from the progeny resulting from the cross of *Guzmania lingulata* 'Panama Red'×*Guzmania squarrosa*, 'Lge. Dark Pink'. With the recognition that this seedling from the cross satisfied the objects of the breeding program, the individual was isolated and set aside for further observation and testing. The resulting selection has been assigned the designation 'Guz 218' for purposes of identification. This plant has been reproduced by tissue culture at Evergem Belgium, and elsewhere, and the clonal specimens resulting have been determined to be identical to the original selection in all distinguishing characteristics. The superior attributes of this plant will be revealed in the botanical descriptions to follow.

SUMMARY OF THE INVENTION

The outstanding attributes of the plant 'GUZ 218' may be summarized as follows:

An overall height of about 22 inches when finished to a stage of full bloom, and having a spread of about 24 inches.

Moderately green, lustrous leaves of strap-like form; rather stiff when compared with those of other marketed Guzmania interspecific hybrids. Largest leaves reach lengths of about 20 inches; have a width of about 1½ inches and are acuminate at the tips. The surfaces of leaves are irregularly striated with light anthocyanin coloration and are anthocyanin shaded at the margins. Leaf arching occurs at the terminal ⅓ of the leaf extension.

Inflorescence is typical in character of hybrids of similar genetic background; bracts range in size from between 6½ by 1½ inches to about 2½ by 1 inch, or less at the terminal portion of the scape or spike. Bracts are of bright conspicuous reddish coloration.

Reproductive organs are enclosed within cylindrical flower corollas. Multiple flowers are generally isolated within the axils formed by the clasping, basal portions of the bracts and occur in groupings. Corollas protrude as bright yellow ovoid pod-like structures (about 2 inches by 3/16 inch) progressively within groups in the axils and progressively from the bottom to the top of the spike. Petals dry and spent flowers mature unevenly, in the sequence of flowering, and dry to brown, scaly capsules.

The compressed lower bracts and the uppermost bracts are ascending; intermediately positioned bracts are splayed relative to the axis of the spike. Bracts are bright red with darkened, pointed tips.

Inflorescence is long lasting. The attractive bright red bract color has a high sheen and the bract coloration is retained under subdued interior lighting conditions for more than two months.

BRIEF DESCRIPTION OF THE VIEW OF THE DRAWING

The single color photograph of the drawing depicts a mature specimen of the plant in top perspective angle in mid to late flowering stage. Illustrated are the mature leaves and the spike; the spike is shown at an angle affording a view of both spent flowers and mature flowers at about stages of anthesis. The relative sizes of the lower, splayed intermediate and terminal bracts can be seen by the angle of the illustration.

The color definitions in the specification to follow have been taken from the *Munsell Limit Color Cascade*. While the colors depicted are believed to be of a high level of color fidelity, the coloration of this plant should be understood to be approximate, and somewhat variable as a function of cultural conditions and horticultural practices. For example, the bract color might slightly fade if the plant is cultured in bright light; the leaf color can be varied by the composition and concentration of fertilizer applied to specimens of the plant.

Parentage: Seedling.

*Seed parent.*—*Guzmania lingulata,* 'Panama Red'.

*Pollen parent.*—*Guzmania squarrosa,* 'Lge. Dark Pink'.

Propagation: Asexual reproduction by tissue culture.

Classification:

Monocot, prennial: Medium, vigorous, upright, spreading, dense, vase formed, and tender. Approximately one year time period from liner to market stage, prolific propensity to develop side-shoots with the general number of leaves and bracts being about 16 when produced for optimum market stage. Overall height 22", including inflorescence. Overall width 24".

Leaves:

*Length.*—18"–20".

*Width.*—1½.

Medium, linear, acuminate, minutely striated and flecked with anthocyanin; margins and tips show some anthocyanin coloration, medium thickness, light to medium green, and smooth. 20-13 in color. (Obverse and reverse ) Leaves somewhat drooping, terminal one-third. Lower leaves stained and striped, —42-9, obverse and reverse more heavily on obverse. Some upper leaves stained at the tips—42-9.

*Margin.*—Smooth.

Flower buds: Tender, medium, long, obtuse, and appressed. Inflorescence branched.

*Primary bracts.*—Bright red in color, clasping 6½"× 1½" decreasing in size to 2½"×1". Upper and lower bracts somewhat ascending. Upper bracts somewhat folded. Lower bracts 41-7 in color, both obverse and reverse. Upper bracts 41-7 in color at the base, blending into 40-10 toward the tips. Upper bracts tipped 43-15 in color, both obverse and reverse.

Flowers: Cylindrical corolla, 2"×3/16" bright yellow, 25-6 in color.

*Sepals.*—26-1 in color; petals scarcely open at anthesis.

Fruit: A 3 chambered capsule, dry when ripe. Seed with pappus.

I claim:

1. A new and distinct Guzmania plant as shown and described herein, characterized particularly as to novelty by the bright red coloration of the bracts, with the lower and uppermost bracts ascending and the intermediately positioned bracts splayed relative to the axis of the spike.

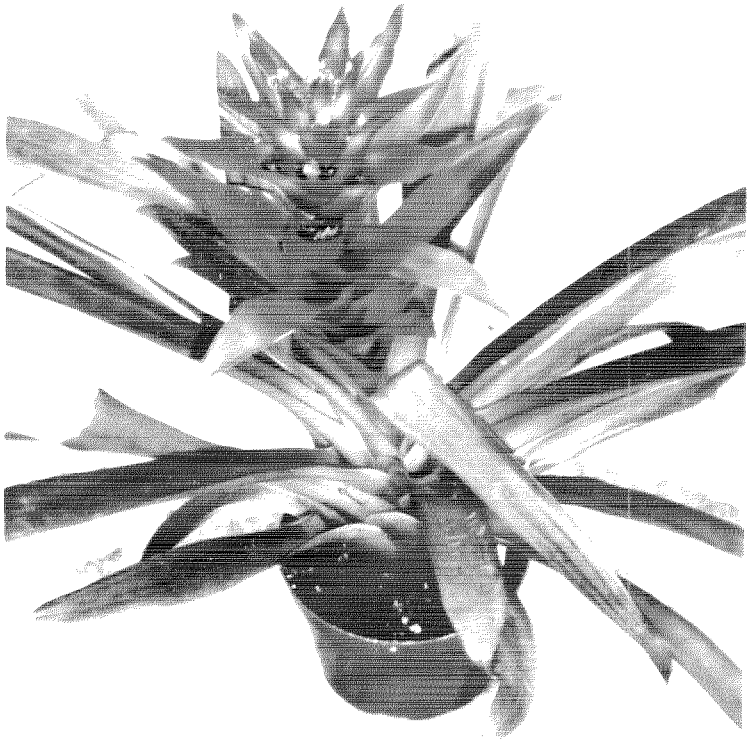

* * * * *